(12) United States Patent
Stroebech et al.

(10) Patent No.: US 9,597,428 B2
(45) Date of Patent: *Mar. 21, 2017

(54) COLLECTING DEVICE FOR BODY FLUIDS

(71) Applicant: Coloplast A/S, Humlebaek (DK)

(72) Inventors: Esben Stroebech, Hoersholm (DK);
Anders Bach, Copenhagen (DK);
Hasse Buus, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 249 days.

This patent is subject to a terminal disclaimer.

(21) Appl. No.: 14/157,543

(22) Filed: Jan. 17, 2014

(65) Prior Publication Data

US 2014/0135720 A1    May 15, 2014

Related U.S. Application Data

(63) Continuation of application No. 12/736,554, filed as application No. PCT/DK2008/050318 on Dec. 18, 2008, now Pat. No. 8,668,678.

(30) Foreign Application Priority Data

Apr. 17, 2008  (DK) .................................. 2008 00561
Apr. 25, 2008  (DK) .................................. 2008 00589

(51) Int. Cl.
*A61F 13/02* (2006.01)
*A61F 15/00* (2006.01)
*A61L 24/00* (2006.01)
*A61F 5/443* (2006.01)
*A61F 5/445* (2006.01)
(Continued)

(52) U.S. Cl.
CPC .......... *A61L 24/0021* (2013.01); *A61F 5/443* (2013.01); *A61F 5/445* (2013.01); *A61L 24/001* (2013.01); *A61L 24/0031* (2013.01); *A61L 24/043* (2013.01); *A61L 24/046* (2013.01); *A61L 24/06* (2013.01); *A61L 28/0034* (2013.01)

(58) Field of Classification Search
None
See application file for complete search history.

(56) References Cited

U.S. PATENT DOCUMENTS 4,191,673 A    3/1980   Wiesman
4,192,785 A    3/1980   Chen et al.
(Continued)

FOREIGN PATENT DOCUMENTS

EP    0019926    12/1980
EP    0413250    2/1991
(Continued)

*Primary Examiner* — Bradley Philips
*Assistant Examiner* — Eric Bryant
(74) *Attorney, Agent, or Firm* — Coloplast Corp., Coloplast A/S; Nick Baumann

(57) ABSTRACT

A body waste collecting device includes a collecting pouch and an adhesive wafer for attachment to the body. The adhesive wafer includes a backing layer, a first adhesive and a second adhesive. The second adhesive includes a polar plasticizing oil or a combination of polar plasticizing oils in the content of above 10% (w/w) of the second adhesive, and at least one polar polyethylene copolymer, where the content of the polyethylene copolymer is 10-50% (w/w) of the second adhesive, and the polyethylene copolymer has a melt flow index below 2 g/10 min (190° C./21.1N).

30 Claims, 1 Drawing Sheet

(51) Int. Cl.
    *A61L 24/04*     (2006.01)
    *A61L 28/00*     (2006.01)
    *A61L 24/06*     (2006.01)

(56) References Cited

U.S. PATENT DOCUMENTS

| | | |
|---|---|---|
| 4,477,325 A | 10/1984 | Osburn |
| 4,775,374 A | 10/1988 | Cilento et al. |
| 5,429,626 A | 7/1995 | Fenton |
| 5,599,601 A * | 2/1997 | Polski ............... A61F 13/58 428/121 |
| 5,834,009 A | 11/1998 | Sawers et al. |
| 6,293,930 B1 | 9/2001 | Brunsgaard et al. |
| 6,482,491 B1 | 11/2002 | Samuelsen et al. |
| 6,531,544 B1 | 3/2003 | Vaughan et al. |
| 8,076,528 B2 | 12/2011 | Lam et al. |
| 2002/0193724 A1* | 12/2002 | Stebbings ............ A61F 13/02 602/54 |
| 2005/0032952 A1 | 2/2005 | Bonfanti et al. |
| 2005/0065486 A1* | 3/2005 | Fattman ............ A61F 5/443 604/332 |
| 2005/0080155 A1 | 4/2005 | Fattman et al. |
| 2006/0020067 A1 | 1/2006 | Brant et al. |
| 2010/0113999 A1* | 5/2010 | Lam ................... A61L 15/425 602/79 |

FOREIGN PATENT DOCUMENTS

| | | |
|---|---|---|
| EP | 0686381 | 12/1995 |
| WO | 02066087 | 8/2002 |
| WO | 2005102229 | 11/2005 |
| WO | 2007082538 | 7/2007 |
| WO | 2007128320 | 11/2007 |
| WO | 2008074333 | 6/2008 |
| WO | 2009006901 | 1/2009 |

\* cited by examiner

COLLECTING DEVICE FOR BODY FLUIDS

FIELD OF THE INVENTION

The present invention relates to a collecting device for attachment to human skin and for collecting bodily waste e.g. an ostomy device.

BACKGROUND

Collecting devices for collecting bodily waste, ostomy appliances, wound or fistulae drainage bandages or devices for collecting urine are usually in the form of a receptacle, e.g. a bag, pouch or tube for receiving the waste, connected to an adhesive wafer that can be attached to the skin of the patient. The wafer is typically in the form of a backing layer coated on the skin-facing surface with an adhesive layer and the wafer may further be provided with an aperture for accommodating the body opening. The size and shape of said aperture can often be adapted individually to fit the anatomy of the patient.

One of the crucial parts of such devices is the adhesive wafer. The wafer should be able to fit leak proof around the body opening, have good adherence to the skin without unintended detachment from the skin, but at the same time be easy to remove again without damaging the skin. Furthermore, the wafer should be able to follow the movements of the body and be comfortable to wear.

When designing a skin adhesive one of the major issues is to keep the skin relatively dry underneath the adhesive to prevent maceration. Maceration occurs when the skin is unable to get rid of moisture from transpiration and outlet from a body opening. This may result in degradation of the skin's barrier function as well as bad adhesion of the device to the skin.

Usually, skin adhesive keeps the skin dry by absorbing moisture. Absorbing particles or hydrocolloids (HC) are mixed into an adhesive matrix in order to absorb moisture from the skin and thereby the skin is kept relatively dry. This technique is well known in the art and forms the basis for most ostomy adhesives that are commercially available see, e.g. U.S. Pat. No. 4,192,785.

To improve the ability of the adhesive wafer to resist leakage, some wafers include a secondary adhesive surrounding a first adhesive center. The first adhesive is positioned adjacent to the output source and the secondary adhesive supplies additional leakage resistance. U.S. Pat. No. 4,775,374 describes an adhesive construction, wherein both the first and the secondary adhesive are hydrocolloid (HC) based. In this adhesive construction, both the first and the second adhesive are sensitive to the output that they are supposed to resist. Additionally, they will both swell when getting in contact with the output. Thus, the failure mechanism is the same for both adhesives and the added protection is limited. Other products, such as the Microskin adhesive with washer sold by Cymed, include a first and a second adhesive where the second outer adhesive is an acrylic adhesive. Acrylic adhesives are known to cause allergic reactions on skin and are therefore problematic. Furthermore, known secondary adhesives strip or otherwise damage the skin upon removal, which can be painful and discomforting to the user.

It has now surprisingly been found that by combining a standard HC adhesive with a polyethylene copolymer based adhesive system, the problem with allergic reactions can be avoided. Furthermore, the standard HC adhesive and the polyethylene copolymer adhesive system are very different in adhesion properties. Thus, the two adhesives characteristics can complement each other to achieve better adhesion than one of the adhesives could achieve alone. Finally, the polyethylene copolymer based adhesive system is non-damaging and less painful to remove, providing a more comfortable secondary adhesive.

SUMMARY OF THE INVENTION

The present invention relates to a body waste collecting device comprising a collecting pouch and an adhesive wafer for attachment to the body, said adhesive wafer comprises a backing layer, a first adhesive and an additional second adhesive, wherein said additional second adhesive comprises a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1N).

BRIEF DESCRIPTION OF THE DRAWING

The invention is disclosed more in detail with reference to the drawings in which.

DETAILED DESCRIPTION OF THE PRESENT INVENTION

Figure 1:
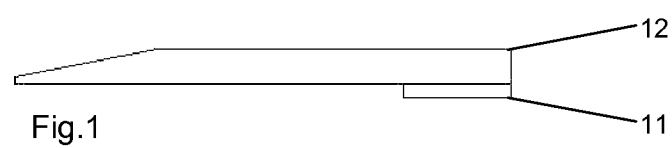
FIGS. 1 to 4 show different embodiments of the invention.

The aim of the invention is to provide a body waste collecting device that includes a first adhesive and an additional second adhesive, wherein said additional second adhesive comprises a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1N).

By body waste collecting device is meant a device being able to collect and hold the output in a collecting item for a predefined time. The holding in place of the device may be obtained by a skin adhesive and the collection may be obtained by a bag.

In an embodiment of the invention a body waste collecting device comprises a collecting pouch and an adhesive wafer for attachment to the body, said adhesive wafer comprises a backing layer, a first adhesive and an additional second adhesive, wherein said additional second adhesive comprises a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1N).

The polyethylene copolymer based adhesive system does not absorb the moisture but rather permeate the water away from the skin surface. Thus, the swelling effect caused by the hydrocolloids will usually not occur. The adhesion is usually obtained by wetting and affinity to the skin.

The additional second adhesive is used for security and protection for the user in order to avoid leakages and to obtain longer wear time.

According to an embodiment of the invention, the first adhesive is located adjacent to the body waste source, usually an ostomy or a fistula.

By located adjacent to is meant that the subject is located close to or even in contact with the other subject.

In one embodiment of the invention, the first adhesive is a hydrocolloid pressure sensitive adhesive.

A standard and conventional hydrocolloid (HC) pressure sensitive adhesive is a skin friendly adhesive that is capable of adhering to the skin, handling perspiration by absorbing the moist and being removable from the skin without essential damage.

A typical pressure sensitive adhesive is based on a polyisobutylene, PIB (adhering substance) and carboxy methyl cellulose, CMC (absorbing media).

A typical HC pressure sensitive adhesive as used today is a highly filled hydrocolloid system with a matrix of polymers that exhibit flow as well as cohesive properties. The hydrocolloids absorb the moisture from perspiration and output from the body and the polymers adhere to the skin through skin polymer affinity and the polymers flow into the small cavities of the skin. The cohesion of the adhesive ensures that erosion is minimised and that the wafer is removed in one piece and that minimal adhesive residues are left at the skin.

The collecting device according to the invention combines the mechanical and adhesive properties of the two kinds of known skin adhesives as described above. A negative effect of the swelling of the hydrocolloid-based skin adhesive is used according to the invention in a beneficial way to provide a sealing effect.

In the use of an ostomy appliance the requirements from the adhesive in the pen stomal area are often different as the use varies within stoma type, body shape, user patterns etc.

When using a hydrocolloid adhesive as the first adhesive according to the invention, the peri stomal area of the adhesive wafer tends to be stiffer resulting in a fixation of the skin in the inner part of the wafer and a more soft and flexible part in the outer zone. The slightly stiffer inner zone is typically obtained from the high filler rate of absorbing particles and choice of adhesive materials that are stiffer than the additional second adhesive.

Such an embodiment according to the invention is especially beneficial when used in cases where very liquid or skin aggressive output is exposed to the inner hole of the adhesive wafer for a long time. A typical example is the use of a 2-piece appliance for ileo ostomy where the adhesive wafer stays on the skin for several days.

The additional second adhesive of the invention comprises a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1N).

According to one embodiment of the invention, the additional second adhesive is produced by mixing a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1N).

In an embodiment of the invention, the final second adhesive in continuous form exhibiting moisture vapour transmission rate of at least 100 g/m$^2$/day for a 150 μm adhesive sheet when measured according to MVTR Test Method.

The primary polymers used in the additional second adhesive are ethylene copolymers. The copolymer should contain a considerable amount of a polar component to get high water permeability. Preferably, the ethylene parts of the copolymer can form crystalline areas that ensure the cohesive strength of the adhesive.

In one embodiment of the invention, the polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof The polar polyethylene copolymer is preferably ethylene vinyl acetate.

The adhesive composition comprising ethylene vinyl acetate may suitably be an adhesive known in the art such as the adhesive composition disclosed, for example in International Patent Application PCT/DK2008/050146.

By polar polymers is meant polymers with water transmission above 50 g/m$^2$/day for a 150 μm film when measured according to MVTR Test Method.

In an embodiment of the invention the ethylene vinyl acetate has a content of at least 40% (w/w) vinyl acetate preferably with 40-80% (w/w) vinyl acetate.

The additional second adhesive should fulfill the Dahlquist's criterion. Preferably, the modulus should be below 100 000 Pa, and for very soft, skin friendly and comfortable adhesive the modulus (G') could be as low as 1-30 kPa measured by DMA at 32° C. and 1 Hz.

It is of great importance, that the additional second adhesive is as soft as possible to ensure a skin friendly material that is comfortable to wear. To get a soft material, the polymer content should be as low as possible. The maximum polymer content of the polar polyethylene copolymer should not exceed 50% (w/w) of the final second adhesive.

Preferably, the polar polyethylene copolymers used in the additional second adhesive should have a molecular structure at a level that results in a melt flow index (MFI) below 2 g/10 min (190° C./21.1N). The melt flow index can be measured by the methods given in ISO 1133 and ASTM D1238.

The advantage of using a polymer with high molecular weight and low MFI is that the high molecular weight polymer can ensure a sufficient high cohesive strength to the additional second adhesive.

By the content of the final second adhesive is meant the percentage in weight of the ingredient in relation to the total weight of the ingredients used in the additional second adhesive.

In an embodiment of the invention, the content of the polar polyethylene copolymer is 10-45% (w/w) of the final second adhesive preferably 15-30%.

In another embodiment of the invention, the polar polyethylene copolymer has a molecular weight above 250,000 g/mol.

In one embodiment of the present invention, the additional second adhesive comprising a polar plasticising oil or a combination of polar plasticising oils in the content of 20-70% (w/w) of the final second adhesive preferably 30-65%.

Polar oils, which may be used in the invention, will generally be those that have good solubility in the polar domains of the polymer, i.e. provide softness without sacrificing too much tensile strength of the polymer. Oils that can support good water vapour permeability are preferred, a 50:50 mix of polymer and oil should have a moisture vapour transmission rate of at least 100 g/m$^2$/day. Examples of such oils are vegetable and animal oils and derivatives thereof. Preferred polar oils are esters, ethers and glycols and particularly preferred is Poly Propylene Oxide, e.g. alpha-butoxy-polyoxypropylene.

The additional second adhesive should preferable contain about or more than 40% plasticising oil to get the optimal softness and skin friendliness.

In one embodiment of the present invention, the additional second adhesive comprising a polar plasticising oil wherein the polar plasticising oil is selected from the group of liquid rosin derivatives, aromatic olefin oligomers, vegetable and animal oils and derivatives, preferable polar oils are esters, ethers and glycols and particularly preferred is poly propylene oxides such as alpha-butoxy-polyoxypropylene.

Furthermore, polypropylene oxide oil contributes to a high permeability of the additional second adhesive.

Some of the additional second adhesives according to the invention contain a minor amount of additional polymer besides the main polymer giving cohesion. This or these additional polymers are added to give tack. These additional polymers are optional and not necessary for all purposes.

In one embodiment of the invention, the additional second adhesive further comprises a low molecular weight polymer, i.e. MFI>2.

The addition of a low Mw polymer to the second adhesive may be an advantage when a lot of moist is present between the additional second adhesive and the skin.

Preferably the total polymer content, including polar polyethylene copolymer and additional polymers (not including oils, tackifier resin etc), should not exceed 50% (w/w) of the final second adhesive.

Additional components may be added to the second adhesive such as tackifier resin, plasticisers and wax.

In one embodiment of the invention, the additional second adhesive further comprises a tackifying resin such as natural, modified or synthetic resins preferably polar resins such as rosins, rosin esters, hydrogenated rosins, hydrogenated rosin esters, and derivatives of such polar resins or pure aromatic monomer resins.

Tackifying resins can be added to control tack in the adhesives, i.e. reduce moduli and increase glass transition temperature.

The content of the tackifying resin is 0-40% (w/w) of the final second adhesive. Preferably the adhesive is substantially free of resin. When the additional second adhesive is containing resin the content of the tackifying resin is preferably 0.1-40% (w/w) of the final second adhesive and more preferably 10-20% (w/w) of the final second adhesive.

In one embodiment of the present invention, the additional second adhesive comprising polar plasticising oils and resin in the content of above 50% (w/w) of the final second adhesive.

In one embodiment of the invention, the additional second adhesive further comprises an additional plasticiser selected from the group of mineral oil, citrate oil, paraffin oil, phatalic acid esters, adepic acid esters (e.g. DOA), and liquid or solid resin.

In another embodiment of the invention, the additional second adhesive further comprises a polyethylene wax.

Other ingredients may be added for auxiliary benefits. This could be antioxidants and stabilisers, fillers for rheology modification or active components like vitamin E or ibuprofen.

In another embodiment of the invention, the additional second adhesive further comprises other ingredients selected from the group of antioxidants, stabilisers, fillers, pigments, flow modifiers, and active ingredients.

In one preferred embodiment of the invention, the additional second adhesive comprises polar active ingredients.

It may be advantageous that the first adhesive comprises absorbent particles. According to an embodiment of the invention, the first adhesive comprises absorbent particles.

The particles may be absorbent particles such as hydrocolloids, microcolloids or super absorbers in order for the composition to absorb moisture from skin.

Microcolloid particles are well-known in the art e.g. from International Publication No. WO 02/066087, which discloses adhesive compositions comprising microcolloid particles. The microcolloid particles may have a particle size of less than 20 microns.

The first adhesive may comprise 1 to 60% w/w of hydrocolloid (HO) or super absorbent particles (SAP) particles, more preferred 30 to 60% w/w particles.

According to a preferred embodiment of the invention, the first adhesive comprises absorbent particles.

According to a preferred embodiment of the invention, the absorbent particles are selected from hydrocolloids, microcolloids and super absorbers.

In an embodiment of the invention, the first adhesive is located on the skin-facing surface of the additional second adhesive.

By the skin-facing surface of the adhesive is meant the side adhering to the skin.

By located is meant where the adhesive is placed on the collecting device and specifies the position of the additional second adhesive or the first adhesive on the collecting device.

In another embodiment of the invention, the additional second adhesive is located on the pouch-facing surface of the adhesive wafer.

By the pouch-facing surface or non-skin-facing surface is meant the side of the adhesive or backing pointing away from the skin (non-bonding side).

According to one embodiment of the invention, the additional second adhesive is located at the outer rim of the adhesive wafer.

By the outer rim portion of the adhesive wafer is meant the portion essentially outside the welding zone or coupling. This portion is less exposed to faeces but has to handle perspiration as well as mechanical exposure due to movements and pull from the bag.

By the inner rim portion of the adhesive wafer is meant the portion in the perianal, peristomal or fistal area. This area of the adhesive is exposed to faeces or exudates as well as perspiration. The properties of the inner rim portion depend on wear time, output type and anatomy among others.

According to an embodiment of the invention, the additional second adhesive is in the form of a ring.

By an adhesive ring is meant an adhesive, essentially surrounding the body opening that needs to be drained or a ring covering the outer or inner rim of the adhesive wafer.

According to one embodiment of the invention, the additional second adhesive is part of a ring such as a half ring covering 180 degrees of a circle.

According to an embodiment of the invention, the first adhesive only covers a part of the additional second adhesive on the skin-facing surface.

According to an embodiment of the invention, the additional second adhesive partly covers the adhesive wafer.

According to another embodiment of the invention, the additional second adhesive partly covers the skin-facing surface of the first adhesive.

According to another embodiment of the invention, the adhesive wafer has a recess for adapting the first adhesive.

The collecting device could be pre-shaped with a recess that fits the first adhesive to be built in the device. A recess could be a cut-out of part of the additional second adhesive.

By adapting is meant that the first adhesive is cast within the collecting device.

According to an embodiment of the invention, the device has an optional backing layer for the first adhesive.

Sealing an opening refers to protection of an opening from output, for example use of a paste around a stoma at the rim of the perineal skin or the rim of a fistula.

According to an embodiment of the invention, the body waste source is a stoma.

According to another embodiment of the invention, the body waste source is a fistula.

According to another embodiment of the invention, the body waste source is an anus.

By a body waste source is meant a natural or artificial body opening such as an anus, a stoma or a fistula.

According to an embodiment of the invention, the collecting device is an ostomy appliance.

According to another embodiment of the invention, the collecting device is a faecal collecting device.

According to another embodiment of the invention, the collecting device is a fistula collecting device.

According to an embodiment of the invention, the collecting pouch is detachable.

According to another embodiment of the invention, the collecting pouch is integrated with the wafer.

The collecting pouch may be detachable from the adhesive wafer by a coupling system or the pouch and the wafer may be integrated with the wafer, e.g. by welding. The two versions are known as one piece or two-piece appliances for ostomy.

DESCRIPTION OF THE PREFERRED EMBODIMENTS

The invention is now explained more in detail with reference to the drawings showing preferred embodiments of the invention.

FIGS. 1 to 4 are all drawings of a side view of the left half of the adhesive wafer according to the invention. All wafers are covered with a backing layer. The skin-facing surface is illustrated in the drawings as the downward side of the wafer and the backing layer is placed on top of the wafer.

FIG. 1 shows an adhesive wafer with a first adhesive (11) and an additional second adhesive (12), where the first adhesive only covers part of the adhesive wafer and is placed on the surface of the skin-facing adhesive wafer. The first adhesive can optionally be covered by a second backing layer placed in between the non-skin-facing side of the first adhesive and the skin-facing side of the additional second adhesive.

Figure 2:

FIG. 2 illustrates a side view of an adhesive wafer with a first adhesive (21) partly covered with an additional second adhesive (22) in the outer rim portion of the wafer.

Figure 3:
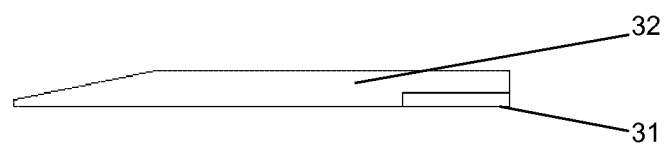

FIG. 3 illustrates a side view of another embodiment of the invention, where an adhesive wafer with an additional second adhesive (32) has a recess for adapting the first adhesive (31).

Figure 4:
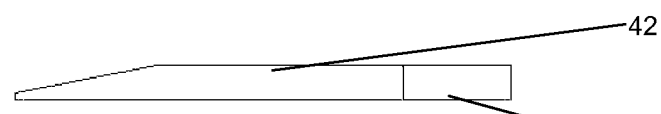

FIG. 4 illustrates a side view of an embodiment of the invention, where an adhesive wafer with a first adhesive (41) is in combination with an additional second adhesive (42) in the inner portion of the adhesive wafer.

Experimental

Laboratory Methods
Method 1: Determination of Moisture Vapour Transmission Rate (MVTR)

MVTR was measured in grams per square meter ($g/m^2$) over a 24 hours period using an inverted cup method.

A container or cup that was water and water vapour impermeable having an opening was used. 20 ml saline water (0.9% NaCl in demineralised water) was placed in the container and the opening was sealed with the test adhesive film. The container was placed into an electrically heated humidity cabinet and the container or cup was placed up side down such that the water was in contact with the adhesive. The cabinet was maintained at 37° C. and 15% relative humidity (RH). The weight loss of the container was followed as a function of time. The weight loss was due to evaporation of water vapour transmitted through the adhesive film. This difference was used to calculate Moisture vapour transmission rate or MVTR. MVTR was calculated as the weight loss pr time divided by the area of the opening in the cup ($g/m^2/24$ h). The MVTR of a material was a linear function of the thickness of the material. Thus, when reporting MVTR to characterise a material, it was important to inform the thickness of the material which MVTR was reported. We used 150 μm as a reference. If thinner or thicker samples were measured, the MVTR was reported as corresponding to a 150 μm sample. Thus a 300 μm sample with a measured MVTR of 10 $g/m^2/24$ h was reported as having MVTR=20 $g/m^2/24$ h for a 150 μm sample because of the linear connection between thickness of sample and MVTR of sample.

Finally, we noted that by using this method, we introduced an error by using a supporting PU film. Utilising the fact, that the adhesive/film laminate was a system of two resistances in series eliminated the error. When the film and the adhesive were homogeneous, the transmission rate may be expressed as:

$$1/P(\text{measured}) = 1/P(\text{Film}) + 1/P(\text{Adhesive})$$

Hence by knowing the film permeability and thickness of the adhesive, it was possible to calculate the true permeability of the adhesive (P(Adhesive)) using the following expression:

$$P(\text{adhesive}) = d(\text{Adhesive})/150\text{micron} * 1/(1/P(\text{measured}) - 1/P(\text{Film}))$$

where d(Adhesive) was the actual measured thickness of the adhesive and P(Film) was the MVTR of the film without any adhesive on and P(measured) was the actual measured MVTR.

Method 2: DMA and Determination of G' and Tan (δ)

The parameters G' and tan (δ) were measured as follows: The adhesives were pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurements were carried out at 32° C.

What is claimed is:

1. A body waste collecting device comprising
   a collecting pouch
   an adhesive wafer for attachment to a body, comprising
     a backing layer;
     a first adhesive having a skin-facing surface configured for direct attachment to the body; and
     a second adhesive having a skin-facing surface configured for direct attachment to the body,
   wherein said second adhesive comprises a polar plasticising oil or a combination of polar plasticising oils in a content of above 10% (w/w) of the second adhesive, and at least one polar polyethylene copolymer, wherein the polyethylene copolymer is 10-50% (w/w) of the second adhesive, and the polyethylene copolymer has a melt flow index below 2 g/10 min (190° C./21.1N).

2. The body waste collecting device according to claim 1, wherein the second adhesive in continuous form exhibiting a moisture vapour transmission rate of at least 100 g/m²/day for a 150 μm adhesive sheet when measured according to MVTR Test Method.

3. The body waste device according to claim 1, wherein the polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

4. The body waste collecting device according to claim 3, wherein the polar polyethylene copolymer is ethylene vinyl acetate.

5. The body waste collecting device according to claim 4, wherein the ethylene vinyl acetate has a content of at least 40% (w/w) vinyl acetate preferably with 40-80% (w/w) vinyl acetate.

6. The body waste collecting device according to claim 1, wherein the polar polyethylene copolymer is 10-45% (w/w) of the second adhesive, preferably 15-30%.

7. The body waste collecting device according to claim 1, wherein the polar polyethylene copolymer has a molecular weight of above 250,000 g/mol.

8. The body waste collecting device according to claim 1, wherein the polar plasticising oil is selected from the group of liquid rosin derivatives, aromatic olefin oligomers, vegetable and animal oils and derivatives, preferable polar oils are esters, ethers and glycols and particularly preferred is poly propylene oxide such as alpha-butoxy-polyoxypropylene.

9. The body waste collecting device according to claim 8, wherein the polar plasticising oil is 20-70% (w/w) of the second adhesive, preferably 30-65%.

10. The body waste collecting device according to claim 1, wherein the second adhesive further comprises a polymer with MFI>2 (190° C./21.1N).

11. The body waste collecting device according to claim 1, wherein the second adhesive further comprises a tackifying resin selected from the group consisting of natural, modified or synthetic resins.

12. The body waste collecting device according to claim 11, wherein the tackifying resin is 0.1-40% (w/w) of the second adhesive, preferably 10-20%.

13. The body waste collecting device according to claim 1, wherein the first adhesive comprises absorbent particles.

14. The body waste collecting device according to claim 13, wherein the absorbent particles are selected from hydrocolloids, microcolloids and super absorbers.

15. The body waste collecting device according to claim 1, wherein the first adhesive is a hydrocolloid pressure sensitive adhesive.

16. The body waste collecting device according to claim 1, wherein the first adhesive is located adjacent to a body waste source.

17. The body waste collecting device according to claim 1, wherein the first adhesive is located on the skin-facing surface of the second adhesive.

18. The body waste collecting device according to claim 1, wherein the second adhesive is located on a pouch-facing surface of the adhesive wafer.

19. The body waste collecting device according to claim 1, wherein the second adhesive is located at an outer rim of the adhesive wafer.

20. The body waste collecting device according to claim 1, wherein the second adhesive is in a form of a ring.

21. The body waste collecting device according to claim 1, wherein the first adhesive partly covers the second adhesive on the skin-facing surface.

22. The body waste collecting device according to claim 1, wherein the second adhesive partly covers the adhesive wafer.

23. The body waste collecting device according to claim 1, wherein the adhesive wafer has a recess for adapting the first adhesive.

24. The body waste collecting device according to claim 1, further comprising a backing layer for the first adhesive.

25. The body waste collecting device according to claim 1, wherein the collecting device is an ostomy appliance.

26. The body waste collecting device according to claim 1, wherein the collecting device is a faecal collecting device.

27. The body waste collecting device according to claim 1, wherein the collecting device is a fistula collecting device.

28. The body waste collecting device according to claim 1, wherein the collecting pouch is detachable.

29. The body waste collecting device according to claim 1, wherein the collecting pouch is integrated with the adhesive wafer.

30. A body waste collecting device comprising
    a collecting pouch
    an adhesive wafer for attachment to a body, comprising
      a backing layer;
      a first adhesive having a skin-facing surface configured for direct attachment to the body; and
    a second adhesive having a skin-facing surface configured for direct attachment to the body,
    wherein said second adhesive comprises a polar plasticising oil or a combination of polar plasticising oils in the content of above 40% (w/w) of a second adhesive, and at least one polar polyethylene copolymer, wherein the polyethylene copolymer is 10-50% (w/w) of the second adhesive, and the polyethylene copolymer has a melt flow index below 2 g/10 min (190° C./21.1N).

* * * * *